(12) United States Patent
Bortinger et al.

(10) Patent No.: US 7,553,795 B2
(45) Date of Patent: Jun. 30, 2009

(54) ACTIVATION OF HIGH SELECTIVITY ETHYLENE OXIDE CATALYST

(75) Inventors: Arie Bortinger, Ridgewood, NJ (US); Andrew D. Schmitz, Hackensack, NJ (US)

(73) Assignee: SD Lizenzverwertungsgesellschaft mbH & Co. KG, Munich (DE)

( * ) Notice: Subject to any disclaimer, the term of this patent is extended or adjusted under 35 U.S.C. 154(b) by 673 days.

(21) Appl. No.: 11/386,028

(22) Filed: Mar. 21, 2006

(65) Prior Publication Data

US 2007/0225511 A1 Sep. 27, 2007

(51) Int. Cl.
*B01J 23/50* (2006.01)
*C07D 301/10* (2006.01)

(52) U.S. Cl. .................. 502/347; 502/348; 549/536

(58) Field of Classification Search .................. 549/536; 502/347, 348
See application file for complete search history.

(56) References Cited

U.S. PATENT DOCUMENTS

| | | | |
|---|---|---|---|
| 2,040,782 A | 5/1936 | Van Peski et al. ............. 260/54 |
| 2,766,261 A | 10/1956 | Landau et al. ........... 260/348.5 |
| 3,962,286 A | 6/1976 | Antonelli et al. ......... 260/348.5 |
| 4,690,913 A | 9/1987 | Nojiri et al. .................. 502/340 |
| 4,786,624 A | 11/1988 | Nojiri et al. .................. 502/226 |
| 6,717,001 B2 | 4/2004 | Evans et al. .................. 549/536 |
| 6,858,560 B2 | 2/2005 | Rizkalla ....................... 502/202 |
| 2004/0110971 A1 | 6/2004 | Evans et al. .................. 549/534 |

FOREIGN PATENT DOCUMENTS

| EP | 1201301 B1 | 5/2002 |
|---|---|---|
| JP | 53033565 B | 3/1978 |
| WO | WO 2004/002954 | 1/2004 |
| WO | WO 2004/002972 | 1/2004 |

*Primary Examiner*—Bernard Dentz
(74) *Attorney, Agent, or Firm*—Scully, Scott, Murphy & Presser, P.C.

(57) ABSTRACT

The invention describes a process for producing a catalyst useful for the epoxidation of an olefin. More particularly, the invention pertains to a catalyst useful for the oxidation of ethylene to ethylene oxide. The catalyst comprises a solid support such as alpha-alumina, which has a catalytically effective amount of silver or a silver-containing compound, and a promoting amount of rhenium or a rhenium-containing compound, and a promoting amount of one or more alkali metals or alkali metal-containing compounds on the surface of the support. To produce a catalyst precursor. The catalyst precursor is contacted with an atmosphere comprising oxygen and steam, which atmosphere is substantially absent of an olefin, to hasten the attainment of peak selectivity in the process of oxidation of ethylene to ethylene oxide.

30 Claims, No Drawings

ACTIVATION OF HIGH SELECTIVITY ETHYLENE OXIDE CATALYST

BACKGROUND OF THE INVENTION

1. Field of the Invention

The invention pertains to a process for producing a catalyst useful for the epoxidation of an olefin. More particularly, the invention pertains to an improved process for producing a catalyst useful for the epoxidation of ethylene to ethylene oxide. The process provides an improved catalyst that can reach its peak selectivity more quickly in the epoxidation process.

2. Description of the Related Art

There is interest in producing a catalyst useful for the epoxidation of olefins. Of particular interest are catalysts for the selective epoxidation of ethylene. These catalysts typically comprise a suitable solid support such as alpha alumina, which has on its surface an amount of silver and at least one promoter that helps to increase selectivity in the epoxidation process. The use of alkali metals and transition metals as promoters for silver catalysts is well known for the production of ethylene oxide by the partial oxidation of ethylene in the vapor phase. Example catalysts are disclosed in U.S. Pat. Nos. 4,010,155; 4,012,425; 4,123,385; 4,066,575; 4,039,561 and 4,350,616.

Such highly selective catalysts contain, in addition to silver, selectivity-enhancing promoters such as rhenium, molybdenum, tungsten or nitrate- or nitrite-forming compounds, as discussed in U.S. Pat. Nos. 4,761,394 and 4,766,105. However, catalysts containing such selectivity-enhancing promoters often give comparatively low selectivities when first operated in the epoxidation process and may require long operating times to attain their peak selectivities.

As a matter of expediency, it is very desirable to shorten the time required for the high-selectivity catalyst to attain its peak selectivity. Elapsed time to peak selectivity can be shortened by conditioning the catalyst prior to use in the epoxidation process. According to WO 2004/002954 and WO 2004/002972, a pre-conditioned catalyst can give peak selectivity almost immediately upon feed introduction. These disclosures require the use of dry gas for catalyst conditioning, without the presence of steam. As specified, the dry gas contains oxygen and may also contain ethylene, carbon dioxide, and an organic halide modifier. Furthermore, the examples in these disclosures illustrate catalyst conditioning inside the reactor used for the epoxidation process, prior to feed introduction, rather than prior to placement in the epoxidation reactor.

The use of steam for conditioning catalysts has been disclosed by Mitsubishi in U.S. Pat. Nos. 4,690,913; 4,786,624 and EP 1201301 B1; wherein, superheated steam is used to treat the support after impregnation with silver and certain promoters. In these cases, steam treatment is used to remove volatile components from the impregnated support to produce the active catalyst. In these examples, steam is not separately used to condition the active catalyst.

The catalyst produced according to the current invention comprises a suitable solid support such as alpha alumina, which has on its surface a catalytically effective amount of silver and suitable promoters, including a selectivity-enhancing rhenium promoter and an alkali metal. The silver and promoters are first deposited on the surface of the support, and then the impregnated support is calcined to produce a catalyst precursor. Thereafter, the catalyst precursor is conditioned by contacting it with an atmosphere comprising a combination of oxygen and steam. The atmosphere during such conditioning is essentially free of olefins such as ethylene. This procedure affords a catalyst that attains peak selectivity in the epoxidation process much faster than a catalyst that has not been subjected to such conditioning in the oxygen and steam atmosphere.

It has now been unexpectedly found that a wet gas treatment of a high-selectivity catalyst, in particular, of a high-selectivity catalyst comprising silver, a rhenium promoter, and an alkali metal promoter, advantageously shortens the time required for the catalyst to reach peak selectivity in the epoxidation process. Furthermore, the activation conditioning step can be carried out in an ex-situ operation. The benefit of this discovery is that the catalyst can be used in the process without the complicated catalyst conditioning required by the prior art.

SUMMARY OF THE INVENTION

The invention provides a process for producing a catalyst useful for the oxidation of ethylene to ethylene oxide which comprises providing a catalyst precursor which precursor comprises a solid support having a surface, a catalytically effective amount of silver or a silver-containing compound on the surface of the support, a promoting amount of rhenium or a rhenium-containing compound on the surface of the support, a promoting amount of one or more alkali metals or alkali-metal-containing compounds on the surface of the support, and thereafter contacting the catalyst precursor with an atmosphere comprising a combination of oxygen and steam, which atmosphere is substantially absent of an olefin.

DETAILED DESCRIPTION OF THE INVENTION

The support employed in this invention may be selected from a large number of solid, refractory supports that may be porous or non-porous. Alumina is well known to be useful as a catalyst support for the epoxidation of an olefin and is the preferred support. The particular alumina may be porous or non-porous. The alumina support may also contain various impurities and additives which may or may not influence the catalytic epoxidation reaction. In the process of making the preferred alumina support, high-purity aluminum oxide, preferably alpha-alumina, is thoroughly mixed with temporary and permanent binders. The temporary binders, known as burnout materials, are thermally decomposable organic compounds of moderate to high molecular weight which, on decomposition, alter the pore structure of the support. The permanent binders are typically inorganic clay-type materials having fusion temperatures below that of the alumina and impart mechanical strength to the finished support. After thorough dry-mixing, sufficient water or other suitable liquid is added to help form the mass into a paste-like substance. Catalyst support particles are then formed from the paste by conventional means such as extrusion. The particles are then dried and are subsequently calcined at an elevated temperature.

U.S. patents which describe the production of alumina supports include U.S. Pat. Nos. 2,499,675, 2,950,169 and 3,172,866. Other patents such as U.S. Pat. Nos. 3,222,129, 3,223,483 and 3,226,191 show the preparation of active aluminas. Methods of making highly porous aluminas are disclosed in U.S. Pat. Nos. 3,804,781, 3,856,708, 3,907,512 and 3,907,982. Alumina carriers having high thermal stability are disclosed in U.S. Pat. No. 3,928,236. Other improvements in making catalyst carriers are discussed in U.S. Pat. Nos. 3,987,155, 3,997,476, 4,001,144, 4,022,715; 4,039,481, 4,098,874 and 4,242,233. Other processes for making supports are described, for instance in U.S. Pat. Nos. 4,575,494, 3,172, 866, 4,356,113, 4,082,697, 4,001,144, 3,856,708, 3,850,849 and 3,526,602.

The support may comprise materials such as alpha-alumina, charcoal, pumice, magnesia, zirconia, titania, kieselguhr, fuller's earth, silicon carbide, silica, silicon carbide, clays, artificial zeolites, natural zeolites, ceramics and combination thereof. The preferred support is comprised of alpha-alumina having a very high purity; i.e., at least 95 wt. % pure, or more preferably, at least 98 wt. % alpha-alumina. The remaining components may include aluminas other than alpha-alumina, such as silica, alkali metal oxides (e.g., sodium oxide) and trace amounts of other metal-containing or non-metal-containing additives or impurities. A wide variety of such supports are commercially available. Suitable alumina carriers are manufactured and generally commercially available from Süd-Chemie Inc., of Louisville, Ky., and Saint-Gobain Norpro, of Stow, Ohio.

Certain types of alpha alumina-containing supports are particularly preferred. These alpha alumina supports have relatively uniform pore diameters and are more fully characterized by having a B.E.T. surface area of from about 0.03 $m^2/g$ to about 10 $m^2/g$, preferably from about 0.05 $m^2/g$ to about 5 $m^2/g$, more preferably from about 0.1 $m^2/g$ to about 3 $m^2/g$; and pore volumes of from about 0.10 cc/g to about 0.85 cc/g, preferably from about 0.25 cc/g to about 0.75 cc/g. Median pore diameters for these supports range from about 0.5 micrometers to about 50 micrometers. The supports may have mono-modal, bimodal or multimodal pore distributions. The surface acidity of the support, as determined by irreversible ammonia sorption at 100° C., is often less than about 2 micromoles per gram of support, preferably less than about 1.5 micromoles per gram of support, and often from about 0.05 to 1.0 about micromoles per gram of support.

Regardless of the character of the support used, it is usually shaped into particles, chunks, pieces, pellets, rings, spheres, wagon wheels, cross-partitioned hollow cylinders, and the like, of a size suitable for employment in fixed-bed epoxidation reactors. Desirably, the support particles may have equivalent diameters in the range of from about 3 mm to about 10 mm and preferably in the range of from about 4 mm to about 8 mm, which are usually compatible with the internal diameter of the tubular reactors in which the catalyst is placed. Equivalent diameter is the diameter of a sphere having the same external surface (i.e. neglecting surface within the pores of the particle) to volume ratio as the support particles being employed.

In general, a suitable catalyst support of the present invention can be prepared by mixing the refractory material, such as alumina, water or other suitable liquid, a burnout material or suitable porosity-controlling agent, and a binder. Burnout materials include cellulose, substituted celluloses, e.g. methylcellulose, ethylcellulose, and carboxyethylcellulose, stearates, such as organic stearate esters, e.g. methyl or ethyl stearate, waxes, granulated polyolefins, particularly polyethylene and polypropylene, walnut shell flour, and the like which are decomposable at the firing temperatures used in preparation of the support. The burnout is used to modify the porosity of the support. It is essentially totally removed during the firing to produce the finished support. Supports of the present invention are preferably made with the inclusion of a bonding material such as silica with an alkali metal compound in sufficient amount to substantially prevent the formation of crystalline silica compounds. Appropriate binders include inorganic clay-type materials. A particularly convenient binder material is a mixture of boehmite, an ammonia stabilized silica sol, and a soluble sodium salt.

A paste is formed by mixing the dry ingredients of the support with water or other suitable liquid, and the paste is usually extruded or molded into the desired shape, and then fired or calcined at a temperature of from about 1200° C. to about 1600° C. to form the support. When the particles are formed by extrusion, it may be desirable to also include extrusion aids. The amounts of extrusion aids required will depend on a number of factors that relate to the equipment used. However these matters are well within the general knowledge of a person skilled in the art of extruding ceramic materials. After firing, the support is preferably washed to remove soluble residues. Washing is most commonly done with water but washing with other solvents or aqueous/non-aqueous solutions can also be beneficial.

In order to produce a catalyst for the oxidation of ethylene to ethylene oxide, a support having the above characteristics is then provided with a catalytically effective amount of silver on its surface. The catalyst is prepared by impregnating the washed or unwashed support with a silver compound, complex or salt dissolved in a suitable solvent sufficient to cause deposition of a silver-precursor compound onto the support. Preferably, an aqueous silver solution is used. After impregnation, the excess solution is removed from the impregnated support, and the impregnated support is heated to evaporate the solvent and to deposit the silver or silver compound on the support as is known in the art.

Preferred catalysts prepared in accordance with this invention contain up to about 45% by weight of silver, expressed as metal, deposited upon the surface and throughout the pores of a porous refractory support. Silver contents, expressed as metal, of from about 1% to about 40% based on the total weight of the catalyst are preferred, while silver contents of from about 8% to about 35% are more preferred. The amount of silver deposited on the support or present on the support is that amount which is a catalytically effective amount of silver, i.e., an amount which economically catalyzes the reaction of ethylene and oxygen to produce ethylene oxide. As used herein, the term "catalytically effective amount of silver" refers to an amount of silver that provides a measurable conversion of ethylene and oxygen to ethylene oxide. Useful silver containing compounds which are silver precursors non-exclusively include silver oxalate, silver nitrate, silver oxide, silver carbonate, a silver carboxylate, silver citrate, silver phthalate, silver lactate, silver propionate, silver butyrate and higher fatty acid salts and combinations thereof.

Also deposited on the support either prior to, coincidentally with, or subsequent to the deposition of the silver is a promoting amount of a rhenium component, which may be a rhenium-containing compound or a rhenium-containing complex. The rhenium promoter may be present in an amount of from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the rhenium metal.

Also deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of silver, support, alkali metal promoters, rhenium component, and optional additional promoters of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity. In the epoxidation process, it may be desirable to intentionally change the operating conditions to take advantage of certain catalytic properties even at the expense of other catalytic properties. The preferred operating conditions will depend upon, among other factors, feedstock costs, energy costs, by-product removal costs and the like.

Suitable alkali metal promoters may be selected from lithium, sodium, potassium, rubidium, cesium or combinations thereof, with cesium being preferred, and combinations of Cs with other alkali metals being especially preferred. The amount of alkali metal deposited or present on the support is to be a promoting amount. Preferably the amount will range from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof. Most preferably the transition metal comprises an element selected from Groups IVA, VA or VIA of the Periodic Table of the Elements. Preferred transition metals that can be present include molybdenum, tungsten, chromium, titanium, hafnium, zirconium, vanadium, thorium, tantalum, niobium, or combinations thereof.

The amount of alkaline earth metal promoter(s) and/or transition metal promoter(s) deposited on the support is a promoting amount. The transition metal promoter may typically be present in an amount of from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the metal. The catalyst may further comprise a promoting amount of one or more sulfur compounds, one or more phosphorus compounds, one or more boron compounds, one or more halogen-containing compounds, or combinations thereof.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount of from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Examples of organic solvents include, but are not limited to, alcohols, in particular alkanols; glycols, in particular alkyl glycols; ketones; aldehydes; amines; tetrahydrofuran; nitrobenzene; nitrotoluene; glymes, in particular glyme, diglyme and tetraglyme; and the like. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range of from about 0.1% by weight up to the maximum solubility afforded by the particular solvent/solubilizing agent combination employed. It is generally very suitable to employ solutions containing from 0.5% to about 45% by weight of silver, with concentrations of from 5 to 30% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e. a silver precursor, rhenium component, alkali metal component, and the optional other promoters, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range of from about 200° C. to about 600° C., preferably from about 200° C. to about 500° C., and more preferably from about 200° C. to about 450° C., at a pressure in the range of from 0.5 to 35 bar. In general, the higher the temperature, the shorter the required heating period. A wide range of heating periods have been suggested in the art; e.g., U.S. Pat. No. 3,563,914 suggests heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Non-limiting examples include nitrogen, argon, krypton, helium, and combinations thereof, with the preferred inert gas being nitrogen. Non-limiting examples of the oxygen-containing oxidizing component include molecular oxygen ($O_2$), $CO_2$, $NO$, $NO_2$, $N_2O$, $N_2O_3$, $N_2O_4$, or $N_2O_5$, or a substance capable of forming $NO$, $NO_2$, $NO_2$, $N_2O_3$, $N_2O_4$, or $N_2O_5$ under the calcination conditions, or combinations thereof, and optionally comprising $SO_3$, $SO_2$, $P_2O_5$, $P_2O_3$ or combinations thereof. Of these, molecular oxygen is a useful embodiment, and a combination of $O_2$ with $NO$ or $NO_2$ is another useful embodiment. In a useful embodiment, the atmosphere comprises from about 10 ppm to about 1% by volume of an oxygen-containing oxidizing component. In another useful embodiment, the atmosphere comprises from about 50 ppm to about 500 ppm of an oxygen-containing oxidizing component.

The impregnated support, which has been calcined as disclosed above, is thereafter contacted with an atmosphere comprising a combination of oxygen and steam, which atmosphere is substantially absent of an olefin, and preferably, completely absent of an olefin. The atmosphere usually comprises from about 2% to about 15% steam by volume, preferably from about 2% to about 10% steam by volume, and more preferably from about 2% to about 8% steam by volume. The atmosphere usually comprises from about 0.5% to about 30% oxygen by volume, preferably from about 1% to about 21% oxygen by volume, and more preferably from about 5% to about 21% oxygen by volume. The balance of the gas atmosphere may be comprised of an inert gas. Non-limiting examples of the inert gas include nitrogen, argon, krypton, helium, and combinations thereof, with the preferred inert gas being nitrogen. The contacting is usually conducted at a temperature of from about 200° C. or higher. In one embodiment the contacting is conducted at a temperature of from about 200° C. to about 350° C. In another embodiment the contacting is conducted at a temperature of from about 230° C. to about 300° C. In another embodiment the contacting is conducted at a temperature of from about 250° C. to about 280° C. In another embodiment the contacting is conducted at a temperature of from about 260° C. to about 280° C. Usually the contacting is conducted for from about 0.15 hour or more. In one embodiment the contacting is conducted for from about 0.5 hour to about 200 hours. In another embodiment the contacting is conducted for from about 3 hours to about 24 hours. In another embodiment the contacting is conducted for from about 5 hours to about 15 hours.

Ethylene Oxide Production

The epoxidation process may be carried out by continuously contacting an oxygen-containing gas with an olefin, which is preferably ethylene, in the presence of the catalyst produced by the invention. Oxygen may be supplied to the reaction in substantially pure molecular form or in a mixture such as air. Molecular oxygen employed as a reactant may be obtained from conventional sources. Reactant feed mixtures may contain from about 0.5% to about 45% ethylene and from about 3% to about 15% oxygen, with the balance comprising comparatively inert materials including such substances as carbon dioxide, water, inert gases, other hydrocarbons, and one or more reaction modifiers such as organic halides. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum. Non-limiting examples of reaction moderators include organic halides such as $C_1$ to $C_8$ halohydrocarbons. Preferably, the reaction moderator is methyl chloride, ethyl chloride, ethylene dichloride, ethylene dibromide, vinyl chloride or mixtures thereof. Most preferred reaction moderators are ethyl chloride and ethylene dichloride. Usually such reaction moderators are employed in an amount of from about 0.5 to 10 ppmv, preferably from 2 to 8 ppmv of the total volume of the feed gas.

A usual method for the ethylene epoxidation process comprises the vapor-phase oxidation of ethylene with molecular oxygen, in the presence of the inventive catalyst, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-45 feet long filled with catalyst. Typical operating conditions for the ethylene epoxidation process involve temperatures in the range of from about 180° C. to about 330° C., and preferably, about 200° C to about 325° C., and more preferably from about 225° C. to about 270° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 0.1-5 seconds. The present catalysts are effective for this process when operated within these ranges of conditions.

The resulting ethylene oxide is separated and recovered from the reaction products using conventional methods. For this invention, the ethylene epoxidation process may include a gas recycle wherein substantially all of the reactor effluent is readmitted to the reactor inlet after substantially or partially removing the ethylene oxide product and the byproducts. In the recycle mode, carbon dioxide concentrations in the gas inlet to the reactor may be, for example, from about 0.5 to 6 volume percent.

The inventive catalysts have been shown to be particularly selective for oxidation of ethylene with molecular oxygen to ethylene oxide. The conditions for carrying out such an oxidation reaction in the presence of the catalysts of the present invention broadly comprise those described in the prior art. This applies to suitable temperatures, pressures, residence times, diluent materials, moderating agents, and recycle operations, or applying successive conversions in different reactors to increase the yields of ethylene oxide. The use of the present catalysts in ethylene oxidation reactions is in no way limited to the use of specific conditions among those which are known to be effective.

For purposes of illustration only, the following are conditions that are often used in current commercial ethylene oxide reactor units: a gas hourly space velocity of 1500-10,000 h$^{-1}$, a reactor inlet pressure of 150-400 psig, a coolant temperature of 180-315° C., an oxygen conversion level of 10-60%, and an EO production rate (work rate) of 2-16 lbs. EO/cu.ft. catalyst/hr. The feed composition at the reactor inlet may typically comprises 1-40% ethylene, 3-12% $O_2$, 2-40% $CO_2$, 0-3% ethane, 0.3-20 ppmv total concentration of organic chloride moderator(s), and the balance of the feed being comprised of argon, methane, nitrogen or mixtures thereof.

The following non-limiting examples serve to illustrate the invention.

EXAMPLE 1

The catalyst support was comprised mainly of α-alumina. It was used in the form of Raschig rings with a 7 mm O.D., a pore volume of about 0.3 cc/g, and a surface area of 0.92 m$^2$/g. Prior to use, the support was washed with an aqueous solution of $NH_4F$ according to procedures disclosed in U.S. Pat. No. 6,858,560, which is incorporated herein by reference. After drying, the washed support was impregnated with a solution containing silver and promoters as described below.

Part 1: Preparation of Stock Silver Solution:

A. Silver Oxalate Paste

Silver oxalate was prepared by mixing 834 g of silver oxide, 442.4 g of oxalic acid dihydrate and 2,808 g of deionized water. The silver oxalate was then separated from the mixture by filtration and was then rinsed with deionized water. The product was recovered as a wet silver oxalate paste.

B. Silver Solution

The silver solution was made by combining 906.9 grams of the silver oxalate paste, 307.9 grams of ethylenediamine and 418.5 grams of deionized water. The ethylenediamine was added slowly to keep the temperature of the reaction mixture below 45° C. Finally, the solution was filtered and found to contain 26.11 wt % Ag.

Part 2: Support Impregnation 9.0 kg of the washed support was placed in a flask and evacuated to 10.0 torr prior to impregnation. To 14.13 kg of the silver solution was added 175.53 g of an 18.87 wt % CsOH aqueous solution, 208.07 g of a 20.56 wt % $LiNO_3$ aqueous solution, 244.71 g of a 5.20 wt % $Re_2O_7$ aqueous solution, 203.58 g of a 5.29 wt % $(NH_4)H_2W_{12}O_{41}$-$xH_2O$ aqueous solution, 195.76 g of a 4.12 wt % $(NH_4)_2SO_4$ aqueous solution, and 8.14 g of deionized $H_2O$. After mixing, the promoted silver solution was aspirated into the evacuated flask to cover the washed support while still maintaining the pressure at about 10.0 torr. The vacuum was released after 15 minutes to restore ambient pressure, hastening complete penetration of the solution into the pores of the washed support. The excess impregnation solution was drained, and the impregnated support was placed in a centrifuge for 1 min at 400 rpm to remove the excess impregnation solution. Finally, the impregnated support was calcined, under nitrogen atmosphere, following the methods disclosed in U.S. Pat. No. 5,504,052, which is herein incorporated by reference, to generate the catalyst precursor.

Part 3: Conditioning of the Catalyst Precursor

Approximately 100 g of the catalyst precursor was dispersed on a wire-mesh tray positioned inside a stainless-steel drum. After making the gas connections, the drum was sealed and then placed in an oven. The treatment gases were preheated to the treatment temperature before passing through the catalyst bed.

After initiating a flow of dry air through the catalyst bed, the oven was heated from room temperature to 200° C. at a heating rate of about 2° C./min and then held at this temperature for 30 minutes. Temperature was then increased to 230° C. at 0.5° C./min and then held at this temperature for 30 minutes. Temperature was finally increased to 260° C. at 0.5° C./min and held at this temperature for 10 minutes. Thereafter, steam was introduced into the gas stream to obtain a gas atmosphere composition of 5 volume % steam in air. These conditions were kept for 6 hours. At the end of this period, steam feed and oven heating were discontinued, and the catalyst was cooled to room temperature under a dry gas air flow.

Part 4: Catalyst Testing

The catalyst was crushed and sized, and about 9 grams of the granulated catalyst was charged into a stainless steel tubular reactor (0.25 inch O.D.). The reactor was heated to control the reaction temperature. The catalyst test was carried out with a feed mixture composed of 7% oxygen, 8% carbon dioxide, 15% ethylene, 0.1 to 10 ppmv ethylene dichloride moderator, and nitrogen as the balance. Pressure was maintained at about 300 psig, and the gas hourly space velocity was 5500 h$^{-1}$.

To start the test, the reactor temperature was raised from 200 to 240° C. at 1° C./h. Thereafter, the temperature was increased to maintain a concentration of about 2.0% ethylene oxide in the reactor effluent gas. The catalyst work rate as defined by kg ethylene oxide produced per hour per m$^3$ of catalyst was about 218. To this work rate, the temperature was kept between 200 to 300° C. Catalyst selectivity is expressed as the mole % ethylene converted to ethylene oxide. A peak selectivity of 88.3% was reached after 129 hours on stream. Catalyst performance is summarized in Table 1.

EXAMPLE 2

The procedures of Example 1 were applied except that the steam concentration was increased from 5% to 10% in the catalyst precursor conditioning step. A peak selectivity of 87.8% was reached after 137 hours on stream. The catalytic performance is summarized in Table 1.

EXAMPLE 3 (COMPARATIVE)

The procedures of Example 1 were applied except that the conditioning was carried out using dry air, without the addition of steam. This comparative example illustrates catalyst performance without the necessary catalyst precursor conditioning in presence of steam and oxygen of the current invention. A peak selectivity of 87.7% was reached after 220 hours on stream. The catalytic performance is summarized in Table 1.

EXAMPLE 4 (COMPARATIVE)

The catalyst precursor of Example 1 was used without any conditioning. This comparative example illustrates catalyst performance without the conditioning step of the current invention. A peak selectivity of 88.3% was reached after 308 hours on stream. The catalytic performance is shown in Table 1.

TABLE 1

Catalyst Performance at peak selectivity

| Example | % Peak Selectivity | Temperature, °C. to reach peak selectivity | Hours to reach peak selectivity |
|---|---|---|---|
| 1 | 88.3 | 259 | 129 |
| 2 | 87.8 | 257 | 137 |
| 3 (Comparative) | 87.7 | 260 | 220 |
| 4 (Comparative) | 88.3 | 258 | 308 |

The results in Table 1 illustrate that peak selectivity is reached much faster when the catalyst precursor is conditioned in a mixture of steam and oxygen according to the invention (Examples 1 and 2) as compared to the same catalyst precursor conditioned in dry air, without steam (Example 3, Comparative), or the same catalyst precursor where the inventive conditioning procedure was completely omitted (Example 4, Comparative). The inventive procedure for catalyst precursor conditioning is especially beneficial for obtaining high ethylene oxide selectivity in a comparatively short period of time.

While the present invention has been demonstrated and described with reference to preferred embodiments, it will be readily appreciated by those of ordinary skill in the art that various changes and modifications may be made without departing from the spirit and scope of the invention. It is therefore intended that the claims be interpreted to cover the disclosed embodiment, those alternatives which have been discussed, and any and all equivalents thereto.

What is claimed is:

1. A process for producing a catalyst useful for the oxidation of ethylene to ethylene oxide which comprises providing a catalyst precursor which precursor comprises a solid support having a surface, a catalytically effective amount of silver or a silver-containing compound on the surface of the support, a promoting amount of rhenium or a rhenium-containing compound on the surface of the support, a promoting amount of one or more alkali metals or alkali-metal-containing compounds on the surface of the support, and thereafter contacting the catalyst precursor with an atmosphere comprising a combination of oxygen and steam, which atmosphere is substantially absent of an olefin.

2. The process of claim 1 wherein the atmosphere is completely absent of an olefin.

3. The process of claim 1 wherein the contacting is conducted at a temperature of from about 200° C. or higher.

4. The process of claim 1 wherein the contacting is conducted at a temperature of from about 200° C. to about 350° C.

5. The process of claim 1 wherein the contacting is conducted at a temperature of from about 230° C. to about 300° C.

6. The process of claim 1 wherein the contacting is conducted at a temperature of from about 250° C. to about 280° C.

7. The process of claim 1 wherein the contacting is conducted for from about 0.15 hour or more.

8. The process of claim 1 wherein the contacting is conducted for from about 0.5 hour to about 200 hours.

9. The process of claim 1 wherein the contacting is conducted for from about 3 hours to about 24 hours.

10. The process of claim 1 wherein the contacting is conducted for from about 5 hours to about 15 hours.

11. The process of claim 1 wherein the contacting is conducted at a temperature of from about 200° C. to about 350° C. for from about 0.5 hour to about 200 hours.

12. The process of claim 1 wherein the contacting is conducted at a temperature of from about 250° C. to about 280° C. for from about 3 hours to about 24 hours.

13. The process of claim 1 wherein the atmosphere comprises from about 2% to about 15% steam by volume and from about 0.5% to about 30% oxygen by volume.

14. The process of claim 1 wherein the atmosphere comprises from about 2% to about 10% steam by volume and from about 1% to about 21% oxygen by volume.

15. The process of claim 1 wherein the atmosphere comprises from about 2% to about 8% steam by volume and from about 5% to about 21% oxygen by volume.

16. The process of claim 1 wherein the atmosphere further comprises an inert gas.

17. The process of claim 1 wherein the atmosphere further comprises nitrogen.

18. The process of claim 1 wherein the support comprises alumina, charcoal, pumice, magnesia, zirconia, titania, kieselguhr, fuller's earth, silicon carbide, silica, silicon dioxide, magnesia, clays, artificial zeolites, natural zeolites, ceramics or combinations thereof.

19. The process of claim 1 wherein the support comprises alumina and the surface is porous.

20. The process of claim 1 wherein the catalyst precursor further comprises a promoting amount of one or more Group IIA metal-containing compounds, one or more transition metal-containing compounds, one or more sulfur-containing compounds, one or more fluorine-containing compounds, one or more phosphorus-containing compounds, one or more boron-containing compounds, or combinations thereof on the surface of the support.

21. The process of claim 20 wherein the Group IIA metal-containing compound comprises beryllium, magnesium, calcium, strontium, barium or combinations thereof.

22. The process of claim 20 wherein the transition metal-containing compound comprises an element selected from Groups IVA, VA, VIA, VIIA and VIIIA of the Periodic Table of the Elements, or combinations thereof.

23. The process of claim 20 wherein the transition metal-containing compound comprises molybdenum, tungsten, chromium, titanium, hafnium, zirconium, vanadium, thallium, thorium, tantalum, niobium or combinations thereof.

24. The process of claim 20 wherein the transition metal-containing compound comprises molybdenum or tungsten or combinations thereof.

25. The process of claim 1 wherein the catalyst further comprises a promoting amount of gallium, germanium, sulfur, phosphorus, boron, halogens or combinations thereof on the surface of the support.

26. The process of claim 1 wherein the alkali metal-containing compound comprises lithium, sodium, potassium, rubidium, cesium or combinations thereof.

27. The process of claim 1 wherein the alkali metal-containing compound comprises cesium.

28. The catalyst produced by the process of claim 1.

29. A process for the oxidation of ethylene to ethylene oxide which comprises the vapor phase oxidation of ethylene with molecular oxygen in a fixed bed, tubular reactor, in the presence of the catalyst produced by the process of claim 1.

30. A process for the oxidation of ethylene to ethylene oxide which comprises the vapor phase oxidation of ethylene with molecular oxygen in a fixed bed, tubular reactor, in the presence of the catalyst produced by the process of claim 20.

* * * * *